United States Patent [19]
Braeuer et al.

[11] Patent Number: 5,354,292
[45] Date of Patent: Oct. 11, 1994

[54] SURGICAL MESH INTRODUCE WITH BONE SCREW APPLICATOR FOR THE REPAIR OF AN INGUINAL HERNIA

[76] Inventors: Harry L. Braeuer, 1007 Cragmore, Seabrook, Tex. 77586; James L. Youngblood, 1514 Neptune La., Houston, Tex. 77062

[21] Appl. No.: 24,934

[22] Filed: Mar. 2, 1993

[51] Int. Cl.$^5$ .................................. A61B 17/00
[52] U.S. Cl. ............................ 606/1; 606/104; 606/151
[58] Field of Search .................. 606/65–67, 606/72–75, 86, 96, 99, 100, 104, 151, 213, 232, 1

[56] References Cited

U.S. PATENT DOCUMENTS

| | | | |
|---|---|---|---|
| 2,248,054 | 7/1941 | Becker | 606/104 |
| 2,671,444 | 3/1954 | Pease, Jr. | |
| 3,334,624 | 8/1967 | Schneider et al. | |
| 3,626,935 | 12/1971 | Pollock et al. | |
| 3,971,670 | 7/1976 | Homsy | |
| 4,347,847 | 9/1982 | Usher | |
| 4,423,721 | 1/1984 | Otte et al. | |
| 4,462,395 | 7/1984 | Johnson | |
| 4,476,861 | 10/1984 | Dimakos et al. | |
| 4,585,458 | 4/1986 | Kurland | |
| 4,655,221 | 4/1987 | Devereux | |
| 4,665,951 | 5/1987 | Ellis | |
| 4,769,038 | 9/1988 | Bendavid et al. | |
| 4,838,884 | 6/1989 | Dumican et al. | |
| 5,042,707 | 8/1991 | Taheri | |
| 5,108,402 | 4/1992 | Chin | |
| 5,116,357 | 5/1992 | Eberbach | 606/213 |
| 5,122,155 | 6/1992 | Eberbach | 606/213 |
| 5,141,515 | 8/1992 | Eberbach | 606/213 |
| 5,147,374 | 9/1992 | Fernandez | 606/151 |
| 5,156,616 | 10/1992 | Meadows et al. | |
| 5,176,692 | 1/1993 | Wilk et al. | 606/213 |
| 5,203,864 | 4/1993 | Phillips | 606/1 |

FOREIGN PATENT DOCUMENTS

| | | | |
|---|---|---|---|
| 0827050 | 5/1981 | U.S.S.R. | 606/104 |
| 1053820 | 11/1983 | U.S.S.R. | 606/104 |

OTHER PUBLICATIONS

Stryker Screw Driver p. 33 of Fracture Appliances Feb. 1, 1947.

*Primary Examiner*—Stephen C. Pellegrino
*Assistant Examiner*—Glenn K. Dawson
*Attorney, Agent, or Firm*—Arnold, White & Durkee

[57] ABSTRACT

A surgical device particularly directed toward the endoscopic repair of inguinal hemas is disclosed. The device includes of a specially adapted surgical mesh and a mechanical means for attaching the surgical mesh to the pubic bone. The surgical mesh is mechanically attached to the pubic bone by an orthopedic screw and the peripheral margins of the mesh either sutured or stapled to the appropriate anatomical structures. The screw is held by the distal end of an inner tube which is positioned inside an outer tube providing an annular space therebetween. The surgical mesh is wrapped around the distal end of the inner tube and the screw and is held in place in the annular space. An actuator tool is placed in the inner tube to provide torque to the screw.

5 Claims, 4 Drawing Sheets

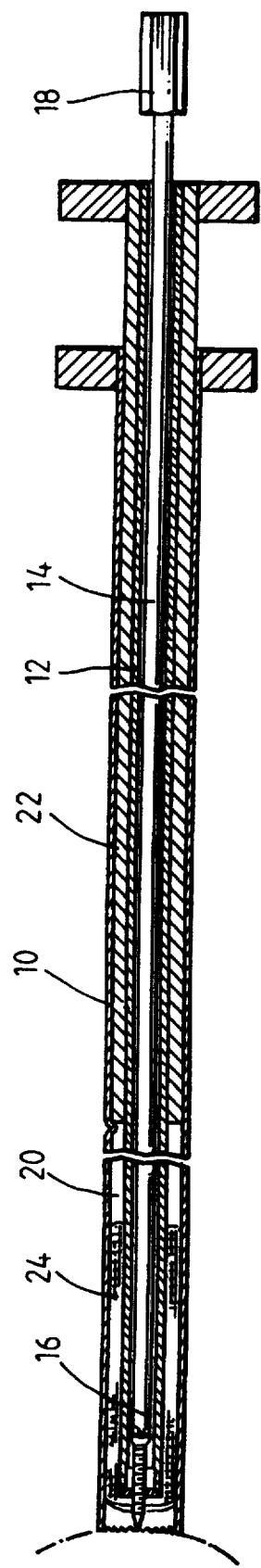
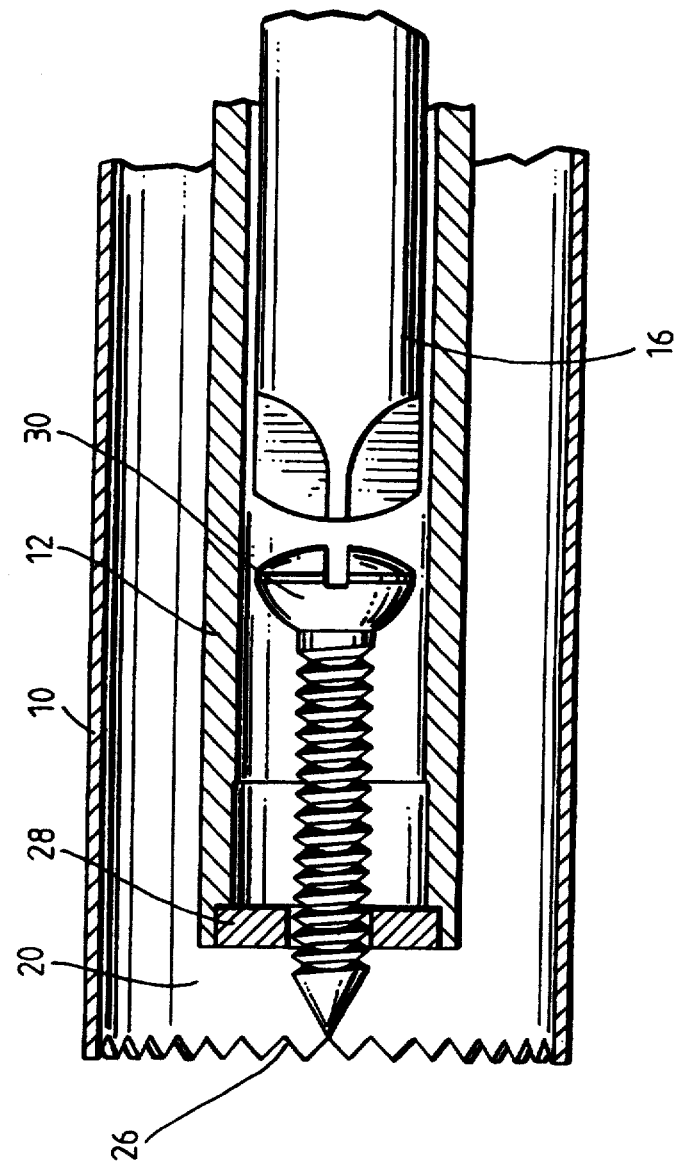

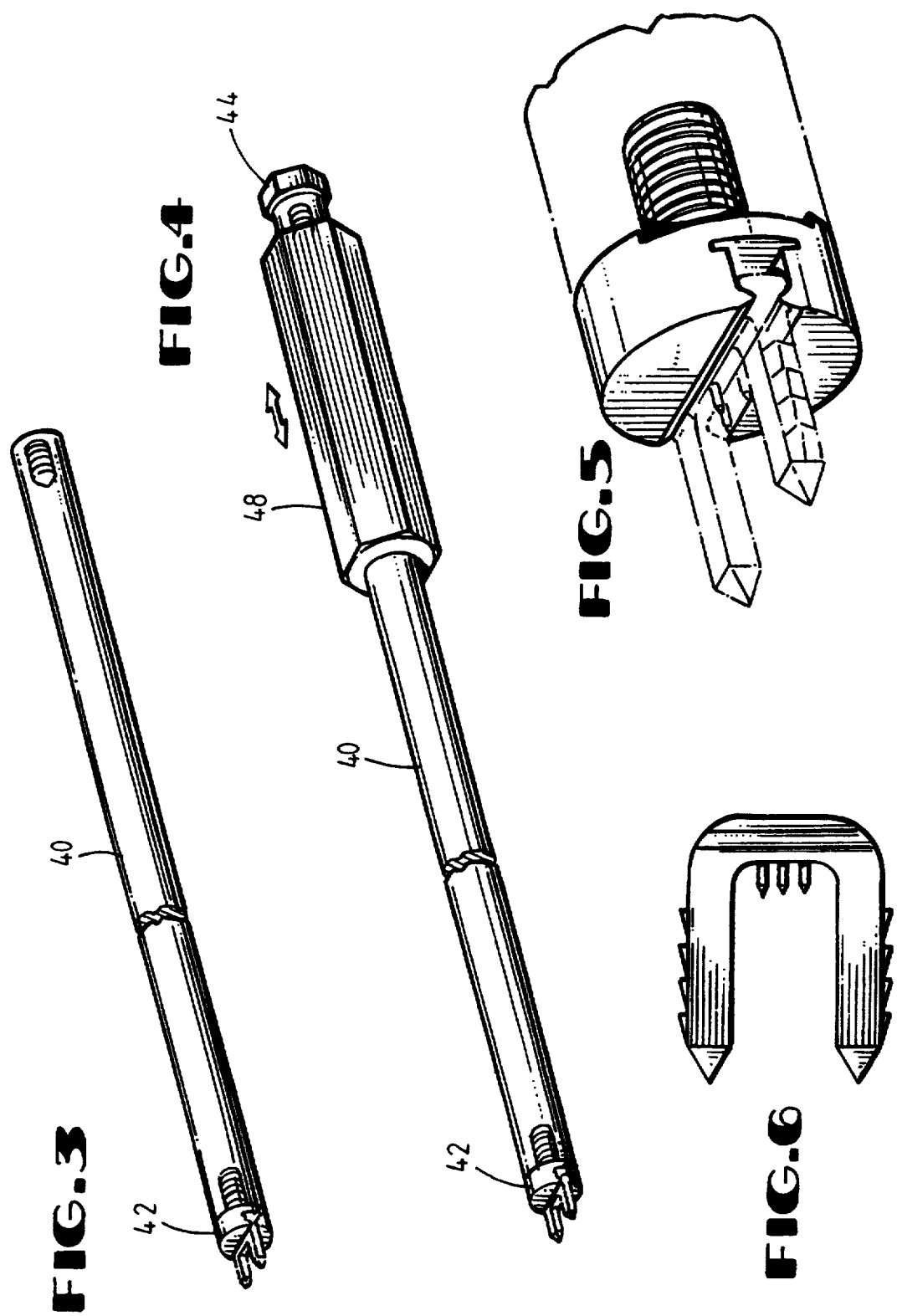

SURGICAL MESH INTRODUCE WITH BONE SCREW APPLICATOR FOR THE REPAIR OF AN INGUINAL HERNIA

FIELD OF THE INVENTION

The present invention relates generally to a surgical instrument and more particularly to a surgical instrument and methods for use in the repair of an inguinal hernia.

BACKGROUND OF THE INVENTION

A hernia is the formation of an opening in the abdominal wall typically accompanied with abdominal tissue and viscera which push through the opening in the abdominal wall. The abdominal wall has several relatively weak regions where hernias tend to occur with greatest frequency. These include: 1) the internal inguinal ring where an indirect hernia occurs, 2) Hesselbach's triangle where a direct hernia occurs, and 3) the femoral ring where a femoral hernia occurs. Each of these defects is considered an inguinal hernia.

A femoral hernia forms in the femoral ring in the iliopubic tract spanning the gap between the inguinal ligament and the pubic bone. This conforms to the space between the femoral vessels and the pubic bone beneath the inguinal ligament.

A direct hernia is the result of weakness of the transversalis fascia that forms the floor of the Hesselbach's triangle. The Hesselbach triangle is bordered by the conjoined tendon and edge of the rectus sheath medially, the inguinal ligament at the base, and the inferior epigastric artery laterally and superiorly. The functional lateral and superior border of the direct hernia is actually the edge of the transversus abdominis muscle.

An indirect inguinal hernia is situated adjacent the direct hernia; the two being separated by the inferior epigastric artery. Unlike the other two hernias, the indirect hernia is the result of a congenital flaw. A sac of peritoneum follows the testis in its descent through the inguinal ring and into the scrotum during development. Normally, the sac seals itself as it passes through the internal ring.

The treatment of an inguinal hernia frequently involves surgery in an effort to repair the defect. In most inguinal hernias, abdominal tissue has pushed through a defect in the abdominal wall. Normally, the abdominal tissue forms a sac lined by the peritoneum with viscera contained in the sac. Treatment requires that the contents of the sac be returned to their normal position in the abdomen and the defect in the abdominal wall surgically repaired by suturing the ruptured fascia at the site of the defect in an effort to close and restore the integrity of the abdominal wall.

Conventional procedures for hernia repair may provide only temporary relief. Typically, they involve stretching of the musculature and ligamentous tissue in order to close the defect. The tissues are sutured while in a stretched configuration which makes the abdominal wall further susceptible to a recurring hernia. Thus, surgical correction of a recurring hernia often results in further degeneration of the involved fascia, muscles, and ligaments.

In an effort to avoid recurring hernias and the resulting progressive deterioration, surgeons commonly use implantable mesh material to repair the defect. A sheet of surgical mesh material, usually polypropylene or Gore-rex TM, is placed over the defect and sutured in place as determined by the surgeon. A single sheet of surgical mesh, generally 3×5 inches in size, may be used to cover all three inguinal defects. Although some hernias may be successfully treated in this manner, others result in failure and recurrence of the hernia.

Endoscopic surgery has been a major improvement in the field of orthopedics, gynecology and general surgery because surgical procedures can be performed in a less invasive manner than previously possible. The surgeon performing an endoscopic procedure will make two to three small incisions rather than one large incision. He then uses an endoscopic camera to view the interior anatomy of the patient. He directs surgical instruments through the incisions not occupied by the camera to the surgical site and performs the surgical procedure. The use of smaller incisions requires that less muscle tissue be cut than when a single large incision is required. Generally, endoscopic procedures significantly reduce the surgical trauma to the patient and consequently reduce the recovery time that the patient requires.

While endoscopic surgery has been quite successful in dealing with many problems, it has not been as successful in the treatment of inguinal hernias. Using the endoscopic pre-peritoneal approach, a single 3×5 inch sheet of mesh may be used to cover all three inguinal detects. A problem arising with the endoscopic or laparascopic approach has been the lack of a predictably effective method of attaching surgical mesh to the tissues proximate to the pubic bone, an area commonly the site of recurrent hernias. Generally, in open surgical procedures for inguinal hernias where surgical mesh has been used, the mesh has been sutured to Cooper's ligament which is attached to the pubic bone. Cooper's ligament is a very tough, fibrous ligament offering good retention of mesh properly sutured to it. Endoscopically, surgical mesh has generally been attached by use of endoscopic staples. Endoscopic staples, however, have not proven to be predictably effective to attach surgical mesh to Cooper's ligament, thereby resulting in recurrence of hernias in the area proximate the pubic bone.

To complete existing procedures using mesh for repairing inguinal hemas, the remaining margins of the surgical mesh have been generally attached to surrounding tissue by endoscopic stapling. This portion of the procedure in endoscopic hernia repair has not proven to be as great a problem because recurrence of a hernia predominately occurs in the region of the pubic bone.

SUMMARY OF THE INVENTION

The present invention in a general aspect comprises a system for installing surgical mesh within the body by mechanically fastening a portion of the mesh to a bone and attaching other portions of the mesh to body pans by suturing or stapling. Mechanical fasteners include surgical screws, staples, and other suitable metallic or plastic devices. In the present invention, surgical screws are preferred for fastening mesh to the pubic bone because of their greater reliability and their ease of installation, especially in endoscopic surgical procedures.

The present invention has particular application in repairing inguinal hernias, including direct, indirect, and femoral hemas. In these instances, a section of surgical mesh is fastened to the pubic bone by means of a mechanical fastener, and it is also fastened by means such as sutures or staples to fascia, muscles and ligaments. The invention has application in both endoscopic and open surgical procedures, but especially in endoscopic procedures. In all such procedures a mechanical fastener is positioned through a cannula proximate a portion of the pubic bone and at a point near the hernia. A portion of a surgical mesh is interposed between the mechanical fastener and the pubic bone, and the fastener is then screwed or otherwise driven into the bone to anchor the mesh. A suitable driving tool is preferably directed through the cannula against the fastener, and a driving force (axial or torsional) then applied to the fastener.

Tools useful in the invention may vary in particular features, depending on such factors as the type of fastener and the surgical procedure employed. In a general aspect, the tools comprise a dispenser or other suitable holder for holding a mechanical fastener in position opposite the pubic bone and proximate an inguinal hernia. The tools also comprise a suitable driving member which is actuatable to drive the fastener from the holder into the pubic bone.

When referring to the use of the present invention, distal is used to mean that portion of the device farthest from the operator and closest to the interior or center of a patient, while proximal is meant to refer to that portion of the device nearest to the operator and farthest from the interior or center of a patient.

In one aspect of the invention, the fastener holder may comprise a cannula or other suitable sleeve member adapted to hold a fastener at one end such that the fastener may be displaced from the sleeve member into the pubic bone. This type of holder has been found to be especially useful in endoscopic procedures with surgical screws as mechanical fasteners. A screw driver with an elongated shank is passed down the sleeve member to engage the head of the screw. The handle of the screw driver protrudes from the opposite (or proximal) end of the sleeve member. The surgeon then operates the handle so as to drive the screw from the sleeve member into the pubic bone. The screwdriver may be operated either manually or mechanically.

In another aspect of the invention, the holder may comprise a specially adapted head which is preferably sized to pass through a cannula or sleeve member so as to be positioned opposite the pubic bone and proximate an inguinal hernia. The head may be adapted to hold and dispense various mechanical fasteners, and it may be used with various driving tools. One especially preferred head comprises a generally cylindrical or disk-like member which is recessed and configured at one end to hold a staple with the ends of the staple facing away from the head, i.e., toward the pubic bone. The recessed portion of the head is configured to hold the staple firmly in position. The head, meanwhile, is made sufficiently flexible such that proximal movement of the central portion of the head relative to the peripheral portion of the head closes the recess sufficiently to grasp the staple. A sharp axial force may then be applied to the proximal end of the head so as to drive the grasped staple into the bone. The axial force may be delivered to the head through a rod which extends from the head to a position where the surgeon may apply an impact to the proximal end of the rod.

As mentioned earlier, it is a primary purpose of the invention to mechanically fasten or anchor a piece of surgical mesh to the pubic bone. To this end, the mesh may simply be placed between the fastener and the bone in a manner similar to conventional open surgery. Preferably, and especially in endoscopic surgery, the mesh is assembled with a mechanical fastener and moved into position along with the fastener. Thus, the mesh is preferably folded or otherwise compressed and held in that condition until ready for application to a hernia. The mesh is then released and expanded to cover the areas to be repaired.

The folded or otherwise compressed mesh is preferably positioned in an annulus surrounding the tool employed to drive a fastener. Thus, a first or outer sleeve through which the driving tool (screwdriver) passes may be coaxial with a larger diameter outer sleeve. An annular chamber is thereby formed between the inner and outer sleeves at the distal end providing an enclosure into which the mesh is packed.

The mesh, itself, may comprise any suitable surgical mesh such as polypropylene, polyethylene, Goretex TM or the like. The mesh preferably is provided with one or more flexible structural members such as stays, struts, seams, or the like which help expand the mesh upon release of the mesh from its place of storage. The structural members approach the mesh itself in flexibility so as to be foldable with the mesh, but are sufficiently strong or have sufficient structural memory to help unfold and position the mesh.

Once a fastener has been driven into the pubic bone, the mesh may be released and expanded simply by moving the apparatus of the invention, i.e., the sleeve or sleeves, away from the bone, such that the fastener drags the mesh from its container.

Positioning of the structural members on the mesh, as well as the shape of the mesh, is preferably such that the mesh conforms to the shape of the patient's anatomy in which the mesh resides. It is desirable that the mesh cover the area of interest and also extend to those ligaments, muscles, or the like to which the mesh is to be sutured or stapled. A preferred mesh design is one which comprises two polypropylene structural members positioned on the mesh such that when the mesh is removed from the cannula, the structural members help urge the mesh into a position conforming to the proximate anatomy.

BRIEF DESCRIPTION OF THE DRAWINGS

FIG. 1A is a longitudinal cross-sectional view of the surgical screw embodiment of the invention.

FIG. 2 is a view in partial section showing the device on a larger scale illustrating the position of the surgical screw and inner sleeve in relation to the outer sleeve.

FIG. 3 is a perspective view of the staple-driver device with a section removed to shorten the length of the drawing.

FIG. 4 is a perspective view of the staple-extractor device with a section removed to shorten the length of the drawing.

FIG. 5 is a perspective view, partly in phantom, showing the head of the staple driver-extractor device in a larger scale shown grasping a staple.

FIG. 6 is a side elevational view of a Richards bone staple.

DETAILED DESCRIPTION OF THE PREFERRED EMBODIMENTS

Figure 7A:
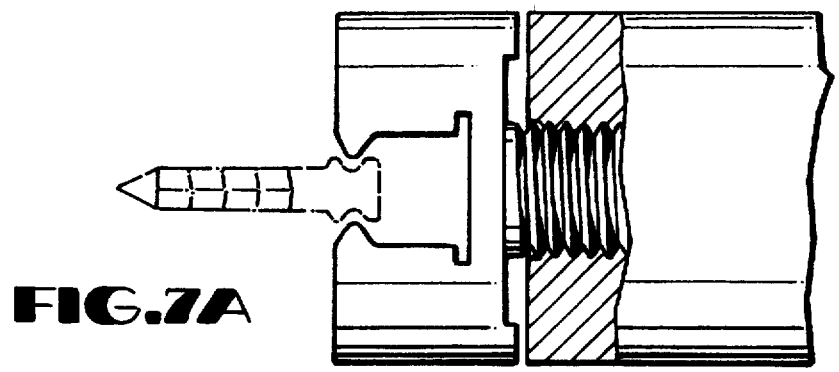
FIG. 7A is a larger scale side elevational view of the head of the staple driver-extractor device showing the device in a staple-release mode.

The present invention exists in several embodiments as illustrated by FIG. 1A through FIG. 6. Referring to the drawings, FIG. 1A illustrates a preferred embodiment of the invention. The apparatus comprises an outer sleeve 10 and an inner sleeve 12. Within the inner sleeve is disposed a shaft 14. The shaft has a first end portion 16 which is configured as a Woodruff head screwdriver. The shaft has a second end portion 18 which has a hexagonal driver attached. Between the outer sleeve and inner sleeve is an annular space 20. Attached to the outer surface of the inner sleeve is a spacer 22 which fills a portion of the annular space. Because the spacer does not extend the entire length of the inner sleeve, the annular space remains between the outer and inner sleeves in the first end portion of the device. Within this annular space is disposed a surgical mesh 24 which is positioned over the end of the inner sleeve.

Figure 1B:
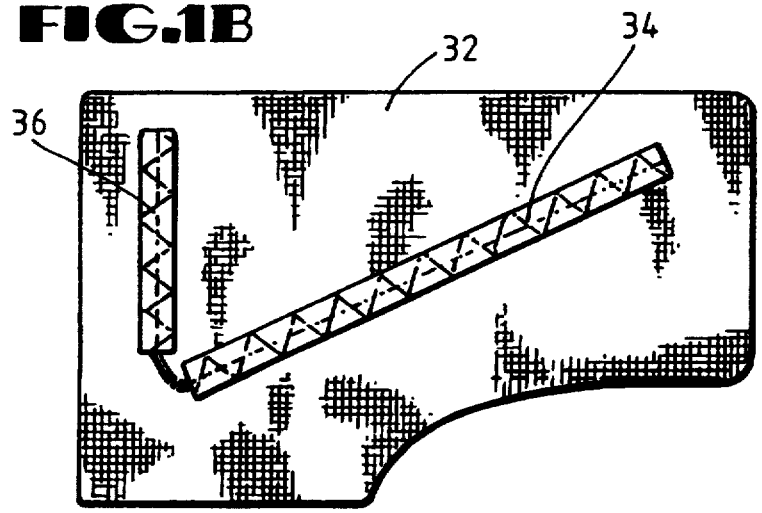
FIG. 1B is a view of the surgical mesh.

FIG. 1B illustrates a specially modified surgical mesh useful in this operation. A standard piece of 3×5 inch surgical mesh is used to fabricate the specially modified surgical mesh. The material typically used is polypropylene; however, Gore-tex TM or other suitable surgical mesh material may also be used. The surgical mesh 32 is properly configured by cutting a portion of the mesh off the lower right hand corner. This cut takes a specific path which begins at about the mid-point of the lower edge of the mesh and continues upward in an arc ending on the right hand edge of the mesh, leaving approximately two-thirds of the mesh on the right hand side. This cut is made to conform the mesh to the blood vessels in the area of the inguinal hernia so that when the mesh is placed, the mesh will not impinge on these vessels. A structural member 34 is made to extend diagonally from the lower left corner to the upper right corner, being set approximately one-half inch in from each corner. Structural member 36 is set parallel to the left edge of the surgical mesh, being positioned approximately one-quarter of an inch in from the left edge of the mesh; one end of the structural member 36 being about one-eighth of an inch in from the top edge of the mesh, and the other end of the structural member 36 being positioned so as to form about a 45° angle with structural member 34. The structural members are made of polypropylene; however, any other material compatible with both the surgical mesh and the human body would be acceptable. The structural members are sewn to the surgical mesh; however, they may also be attached by other acceptable means.

As previously stated, the structural members are disposed on the surface of the surgical mesh in the approximate form of a 45° angle. When positioned within the first end portion of the surgical device, an orthopedic screw preferably goes at the apex of the angle formed by the structural members.

When the surgical mesh is mechanically fastened to a patient's pubic bone by means of the orthopedic screw, the inner sleeve and the outer sleeve are removed from the surgical area, allowing the surgical mesh to unfold aided by the structural members.

FIG. 2 is an enlargement of the first end portion of the device of FIG. 1A. The first end portion of the outer sleeve is preferably configured with serrations 26 for placement against a patient's pubic bone. As previously stated, an annular space 20 exists between the outer sleeve 10 and the inner sleeve 12 housing a surgical mesh which is not illustrated here. The first end portion of the inner sleeve is adapted to receive a screw retaining means 28. The screw retaining means may be a washer or other device configured for retaining a screw. In a preferred embodiment, the washer is polypropylene; however, it can be of another material compatible inside the human body. (A second larger washer, not shown, may be used to secure the flexible mesh over a larger area.) The screw retaining means retains a sharpened, Woodruff orthopedic screw 30. In use, the first end portion of the shaft 16 configured as a Woodruff screwdriver engages the head of the surgical screw and drives the screw into the pubic bone of the patient. As previously stated, the surgical mesh which resides within the annular space in the first end portion of the device is draped over the first end portion of the inner sleeve and also over the sharpened end of the orthopedic screw. When the screw is driven into the pubic bone of the patient, the surgical mesh is also engaged and thereby attached to the patient's pubic bone, thus firmly and predictably attaching the surgical mesh to the pubic bone.

FIGS. 3-6 illustrate a second embodiment of the invention which is preferably used to drive and extract staples. FIG. 4 shows a preferred form of this embodiment, which is particularly suited for extracting staples, but may also be used for driving staples. This form of the embodiment comprises a shaft 40; a slide hammer 48 (used only for extracting staples); a hexagonal end cap 44, a suitable flat-topped capscrew or the like; and a staple grasping device or dispenser 42. The shaft 40 in this form of the embodiment is generally about 18 inches in length, exclusive of the end cap 44 and the staple grasping device 42. The shaft of the embodiment in FIG. 4 is longer than the embodiment shown in FIG. 3. The purposes for the longer shaft are to accommodate the slide hammer 48, allowing adequate length for its effective use, and to accommodate larger patients where the shorter shaft would tend to prevent effective use of the device.

A similar form of the device is shown in FIG. 3. This form is aimed at driving staples. This latter form comprises the shaft 40, in this case about 12 inches long; and the staple grasping device 42. It may be desired to use the end cap 44 (not shown in FIG. 3, but illustrated in FIG. 4) with this form of the device. The end cap offers two advantages: (1) a broader surface to strike when driving the staple into place; and (2) the tool is less likely to roll while on the surgical tray.

FIG. 5 illustrates the staple grasping device with a Richards orthopedic bone staple grasped in the jaws of the device.

FIG. 6 is a side elevational view of a Richards bone staple.

FIG. 7A illustrates the staple grasping device in its staple releasing mode. The staple grasping device has a first end portion which is flat and disk-shaped. The first end portion possesses a transverse slot which is configured to grasp a staple. The staple grasping device possesses a second end portion which is specially adapted to aid in the grasping of the staple and also possesses a threaded member which allows the device to be releasably attached to the shaft.

Figure 7B:
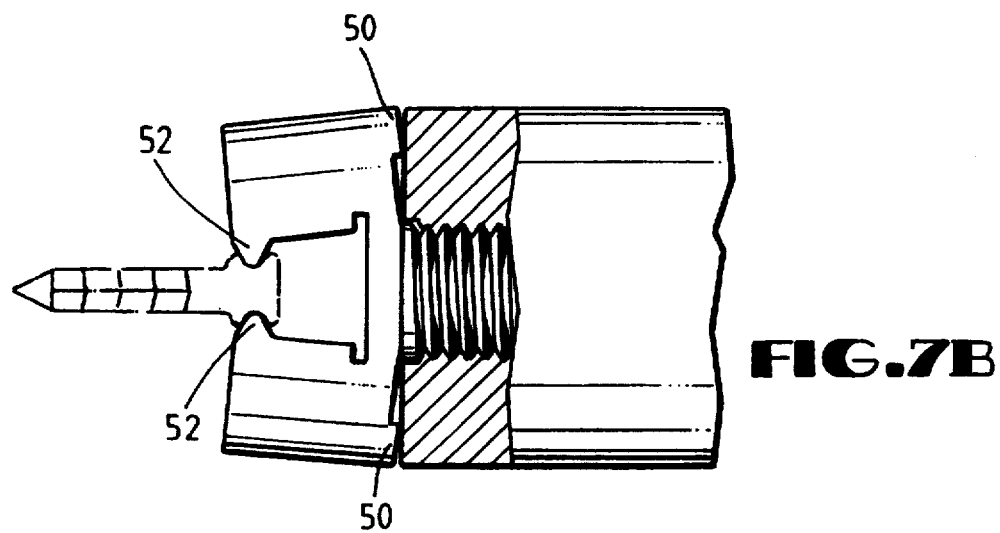
FIG. 7B is a larger scale side elevational view of the staple driver-extractor device showing the device in a staple-grasping mode (deflection exaggerated for clarity).

FIG. 7B illustrates the staple grasping device in its grasping mode. When the surgical device is screwed tightly onto the shaft, the lands 50 contact the first end portion of the shaft. Then as the device is screwed tighter onto the shaft, the central portion of the staple grasping device is pulled toward the shaft, causing the device to flex and the lobes 52 to grasp the staple. To release the staple, the pressure on the staple grasping device is relieved by loosening the staple grasping device from the shaft.

During normal operation, the surgical mesh illustrated in FIG. 1B is positioned at the surgical site separately from the staple driving device. Once in place, the staple driving device securely grasping a Richards bone staple is placed with the sharpened points of the surgical staple positioned at the apex of the angle formed by the structural members as previously described. Using a surgical hammer, the orthopedic staple is hammered into place. Thusly, the surgical mesh is firmly and predictably attached to the patient's pubic bone. Then using the purchase of the staple, the shaft is unscrewed slightly from the staple grasping device, allowing the staple grasping device to return to its release mode. Then, the device is removed from the patient.

Following the attachment of the surgical mesh to the patient's pubic bone, the peripheral edges of the surgical mesh are attached to appropriate anatomical structures of the patient by means of either sutures or staples.

Figure 8A:
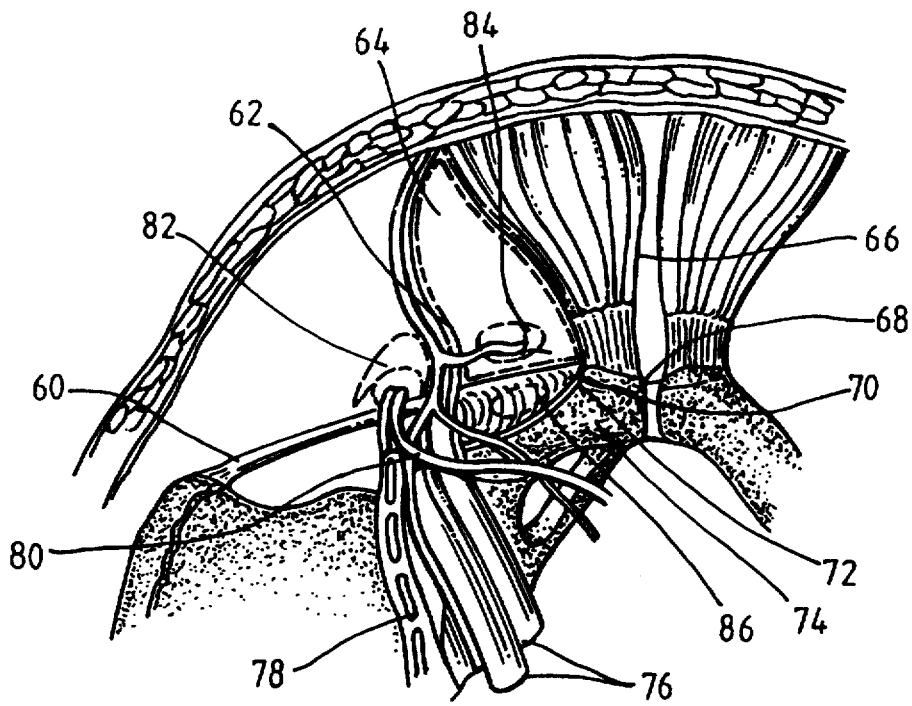
FIG. 8A illustrates inguinal anatomy as viewed through a laparascope.

FIG. 8A illustrates the anatomy relevant to practicing the present invention as viewed through an endoscope. The parts of the anatomy include the ilioinguinal ligament 60, epigastric vessels 62, Hesselbach's triangle 64, rectus abdominis muscle 66, pubic tubercle 68, lacunar ligament 70, Cooper's ligament 72, pubic ramus 74, iliac vessels 76, testicular vessels 78 and vas deferens 80. Of particular interest are the sites of an indirect hernia 82, a direct hernia 84, and a femoral hernia 86.

Figure 8B:
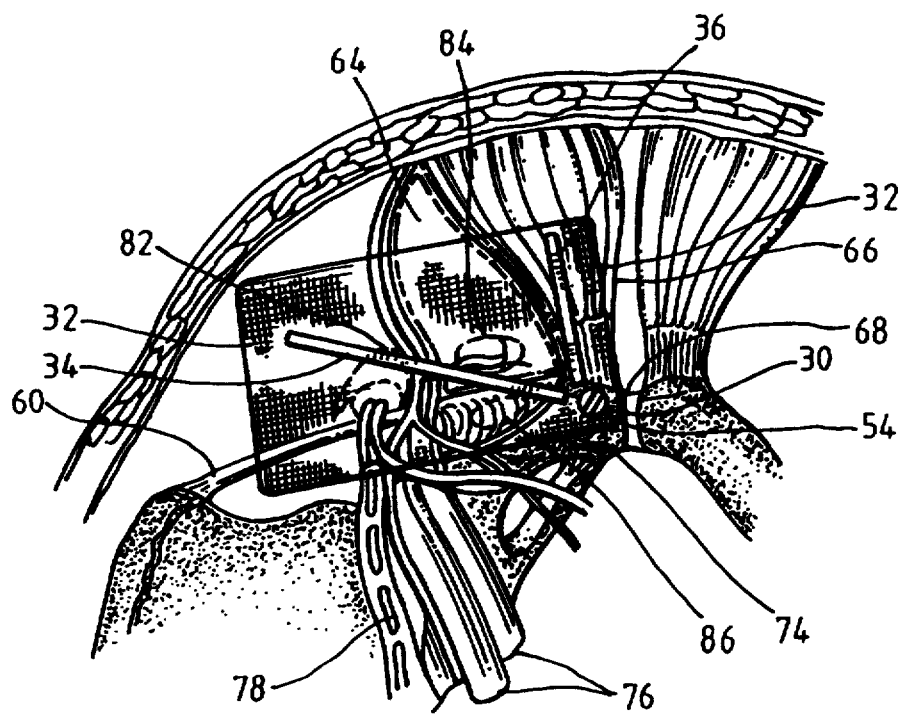
FIG. 8B illustrates the placement of the surgical mesh attached by surgical screw to the pubic bone overlying three hernia defects.

FIG. 8B illustrates the placement of the surgical mesh 32 over three hernia defects and attached to the pubic bone by an orthopedic screw. The diagonal structural member 34 is positioned over Hesselbach's triangle 64 and the internal inguinal ring (indicated by the site of an indirect hernia) 82. The vertical structural member 36 extends toward the rectus abdominis muscle 66. The mesh between the structural members protects the usual site for a direct hernia 84. The mesh lateral to the diagonal structural member protects the usual sites for both indirect 82 and femoral hernias 86. The surgical screw 54 is shown fastened to the pubic ramus 74.

The present invention may be used in either open or endoscopic surgery.

Referring to FIGS. 8A and 8B and using an open surgical method, following the reduction of the inguinal hernia, a specially adapted piece of surgical mesh is mechanically fastened to the patient's pubic bone. This may be done using either of the embodiments of the invention described above. The surgical mesh 32 may be positioned so that the first and longest structural member is positioned over Hesselbach's triangle 64 and the internal ring 82. Once attached to the patient's pubic bone, the structural members 34 and 36 attached to the surgical mesh tend to help conform the mesh to the patient's anatomy in the region of the hernia.

The peripheral margins of the surgical mesh may then be sutured or stapled to the appropriate anatomy. The segment of the surgical mesh proximate the first and longest structural member may be sutured or stapled to the iliopubic tract (not shown) lateral to the internal ring 82. The portion of the surgical mesh proximate the mechanical fastener may be sutured or stapled to Cooper's 72 or Poupart's (not shown) ligament. A third portion of the surgical mesh proximate the second structural member attached to the surgical mesh may be sutured or stapled to the undersurface of the rectus abdominis muscle 66. Finally, a fourth portion of the surgical mesh, being the superior edge of the mesh, may be sutured or stapled to the undersurface of the transverse abdominis arch (not shown). When suturing is preferred, Ethicon 2-0 suture may be used for attaching the surgical mesh, using the interrupted method. The surgery may then be completed in traditional fashion.

The endoscopic method is a bit more complex, as will be indicated by the following example. The patient is first administered general anesthesia and properly prepped and draped. A 1 cm. incision is then made in the inferior aspect of the umbilicus and a Verres needle is inserted into the peritoneal cavity. The peritoneal cavity is insufflated to 14 min. mercury with $CO_2$, the needle removed and a 10/12 min. trocar sheath inserted into the peritoneal cavity. The endoscopic camera is positioned through the trocar sheath.

Two incisions are made at the edge of the rectus abdominis muscle parallel to the umbilicus on the fight and left sides. The incisions are about 1 cm. in length and are preparatory to insertion of trocar sheaths. Using monitor vision, a 10/12 min. trocar sheath is inserted into each incision. The patient is placed in the Trendelenberg position and fight direct and indirect inguinal hernias are observed.

A grasping forcep is placed in the left sheath and an endoscopic scissor in the fight sheath. An incision is made in the peritoneum lateral and superior to the internal ring 82 and extended transversely across to the medial umbilical ligament (not shown) and from there inferiorly to the pubic bone. The peritoneum is immobilized by the avulsion technique, thereby reducing the inguinal sac and thus exposing the femoral vessels (not shown), the internal ring 82, Hesselbach's triangle 64, and the pubic bone.

A specially adapted 3×5 inch polypropylene mesh 32 and surgical screw 54 contained within the previously described surgical device are inserted through the umbilical 10/12 min. trocar sheath and placed against the pubic bone at the upper rami (represented by position of screw 54). The screw is driven into the bone and the device withdrawn, thus unfolding the specially adapted 3×5 inch polypropylene mesh. The long diagonal structural member of the mesh is positioned diagonally across the Hesselbach's triangle 64 and internal ring 82. Using an endostaple device, the mesh proximate to the first and longest structural member is stapled to the iliopubic tract (not shown) lateral to the internal ring. The margin of the surgical mesh proximate to the second structural member is then stapled to the undersurface of the rectus abdominis muscle 66 superiorly. The superior edge of the mesh is stapled to the undersurface of the transverse abdominis arch (not shown).

The previously dissected fold of the peritoneum (not shown) is placed over the entire mesh and reperitonealized by stapling the cut edges of the peritoneum to the upper portion of the previous peritoneal incision.

Closure is done in traditional fashion.

Although several preferred embodiments have been described in a fair amount of detail, it is understood that such detail has been for purposes of clarification only. Various modifications and changes will be apparent to one having ordinary skill in the art without departing from the spirit and scope of the invention as hereinafter set forth in the claims.

What is claimed is:

1. Apparatus for repairing an inguinal hernia, comprising:
   a) an outer sleeve including a distal end positionable within a patient proximate an inguinal hernia and the pubic bone, and a proximal end adapted to extend through an incision in the patient;
   b) an inner sleeve having distal and proximal ends corresponding to said distal and proximal ends of said outer sleeve, said inner sleeve positioned within the outer sleeve and defining an annular space between said outer sleeve and said inner sleeve:
   c) a piece of surgical mesh stored within said annular space, a portion of said piece of surgical mesh covering said distal end of said inner sieve:
   d) a surgical fastener positioned proximate said distal ends of said inner and outer sleeves and coupled to said piece of surgical mesh, said surgical fastener being actuatable to fasten said piece of surgical mesh to the pubic bone; and
   e) a fastener actuating tool inserted within said inner sleeve, said fastener actuating tool having a distal end configured to engage said surgical fastener, and a proximal end adapted to receive and transmit actuating power to said surgical fastener to fasten said piece of surgical mesh and said surgical fastener to the cubic bone.

2. The apparatus of claim 1, wherein said surgical fastener comprises a surgical screw.

3. The apparatus of claim 2, which further comprises a supporting member at said distal end of said inner sleeve to support said surgical screw prior to actuation by said fastener actuating tool.

4. An apparatus for repair of an inguinal hernia, comprising:
   a) an outer sleeve having a distal end portion positionable opposite an inguinal hernia and a proximal end portion adapted to extend through an incision in a patient;
   b) an inner sleeve positioned within said outer sleeve and defining an annular space between said inner sleeve and said outer sleeve, said inner sleeve having a distal end portion proximate said distal end portion of said outer sleeve;
   c) a surgical screw protruding from said distal end portion of said inner sleeve and adapted to be driven from said inner sleeve; and
   d) a surgical mesh positioned within said annular space and extending over said distal end portion of said inner sleeve and said surgical screw.

5. Apparatus for repairing an inguinal hernia, comprising:
   a first cannula having a distal end and a proximal end, said distal end holding of a surgical screw with a pointed end of said surgical screw directed outward from said distal end;
   a piece of surgical mesh covering said distal end of said first cannula and said pointed end of said surgical screw held within said distal end of said first cannula;
   a second cannula adapted to receive said distal end of said first cannula and defining an annular space therebetween, said annular space containing said piece of surgical mesh: and
   a screw driver positioned within said first cannula and having two ends, said screw driver adapted at one end to engage a head of said surgical screw held within said distal end of said first cannula, and adapted at another end to extend beyond said proximal end of said first cannula, said other end being further adapted to receive and transmit actuating power to said surgical screw.

* * * * *

UNITED STATES PATENT AND TRADEMARK OFFICE
CERTIFICATE OF CORRECTION

PATENT NO. : 5,354,292
DATED : October 11, 1994
INVENTOR(S) : Harry L. Braeuer and James L. Youngblood It is certified that error appears in the above-indentified patent and that said Letters Patent is hereby corrected as shown below:

Column 9, Claim 1, line 25, please delete the word "sieve" and replace with --sleeve--.

Signed and Sealed this

Sixteenth Day of May, 1995

Attest:

BRUCE LEHMAN

*Attesting Officer*     *Commissioner of Patents and Trademarks*